United States Patent [19]

Takaya et al.

[11] Patent Number: 4,559,334

[45] Date of Patent: Dec. 17, 1985

[54] 7-SUBSTITUTED-3-VINYL-3-CEPHEM COMPOUNDS AND PROCESSES FOR PRODUCTION OF THE SAME

[75] Inventors: Takao Takaya, Kawanishi; Hisashi Takasugi, Osaka; Takashi Masugi, Ikeda; Hideaki Yamanaka, Hirakata; Kohji Kawabata, Osaka, all of Japan

[73] Assignee: Fujisawa Pharmaceutical Co., Ltd., Osaka, Japan

[21] Appl. No.: 543,880

[22] Filed: Oct. 20, 1983

Related U.S. Application Data

[63] Continuation-in-part of Ser. No. 428,970, Sep. 30, 1982, abandoned, which is a continuation-in-part of Ser. No. 205,334, Nov. 10, 1980, Pat. No. 4,409,214.

[30] Foreign Application Priority Data

Aug. 26, 1983 [GB] United Kingdom ................. 8323034

[51] Int. Cl.$^4$ ................. C07D 501/24; A61K 31/545
[52] U.S. Cl. .................................... 514/202; 544/22; 544/23
[58] Field of Search .................... 544/22, 23; 424/246; 514/202

[56] References Cited

U.S. PATENT DOCUMENTS

| | | | |
|---|---|---|---|
| 3,994,884 | 11/1976 | Weir | 544/22 |
| 4,107,431 | 8/1978 | Clark et al. | 544/16 |
| 4,264,595 | 4/1981 | Numata et al. | 544/22 |

*Primary Examiner*—Donald G. Daus
*Assistant Examiner*—Robert Benson
*Attorney, Agent, or Firm*—Oblon, Fisher, Spivak, McClelland & Maier

[57] ABSTRACT

The invention relates to novel compounds of high antimicrobial activity of the formula:

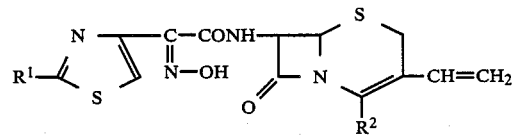

in which
R$^1$ is amino or a protected amino group, and
R$^2$ is carboxy or a protected carboxy group, and a pharmaceutically acceptable salt thereof.

20 Claims, No Drawings

7-SUBSTITUTED-3-VINYL-3-CEPHEM COMPOUNDS AND PROCESSES FOR PRODUCTION OF THE SAME

This application is a continuation-in-part of application Ser. No. 428,970, filed Sept. 30, 1982 now abandoned, which in turn is a continuation-in-part of application Ser. No. 205,334, filed Nov. 10, 1980, now U.S. Pat. No. 4,409,214.

The present invention relates to novel 7-substituted-3-vinyl-3-cephem compounds and a pharmaceutically acceptable salt thereof.

More particularly, it relates to novel 7-substituted-3-vinyl-3-cephem compounds and a pharmaceutically acceptable salt thereof, which have antimicrobial activity, to processes for the production of the same, to a pharmacetical composition comprising the same, and to a method for the treatment of infectious diseases caused by pathogenic microorganisms comprising administering the same to infected human being or animals.

Accordingly, one object of the present invention is to provide novel 7-substituted-3-vinyl-3-cephem compounds and a pharmaceutically acceptable salt thereof, which are highly active against a number of pathogenic microorganisms and are useful as antimicrobial agents, especially for oral administration.

Another object of the present invention is to provide processes for the production of novel 7-substituted-3-vinyl-3-cephem compounds and a salt thereof.

A further object of the present invention is to provide a pharmaceutical composition comprising, as an active ingredient, said 7-substituted-3-vinyl-3-cephem compounds and a pharmaeutically acceptable salt thereof.

Still further object of the present invention is to provide a method for the treatment of infectious diseases caused by pathogenic microorganisms which comprises administering said 7-substituted-3-vinyl-3-cephem compounds and a pharmaceutically acceptable salt thereof to the infected human being or animals.

The 7-substituted-3-vinyl-3-cephem compounds according to this invention are novel and can be represented by the following general formula (I).

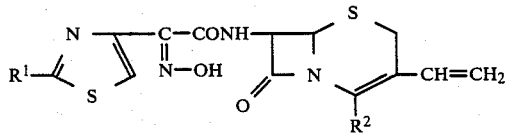

in which
R$^1$ is amino or a protected amino group, and
R$^2$ is carboxy or a protected carboxy group.

It is to be understood that the term "syn isomer" used in the present specification means the compound (I) having the stereospecific partial structure of the formula:

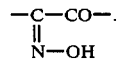

Suitable pharmaceutically acceptable salts of the object compound (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

The object compound (I) or a pharmaceutically acceptable salt thereof of this invention can be produced by the processes illustrated below.

Process 1:

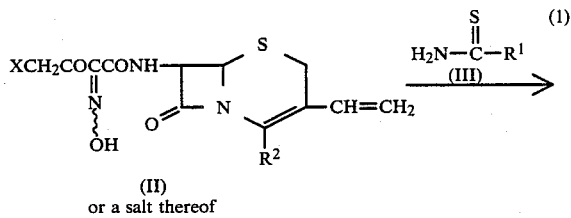

(II)
or a salt thereof (I)
or a salt thereof

Process 2:

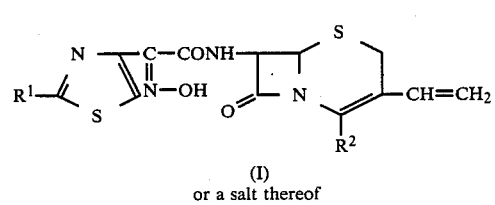

(Ia)
or a salt thereof

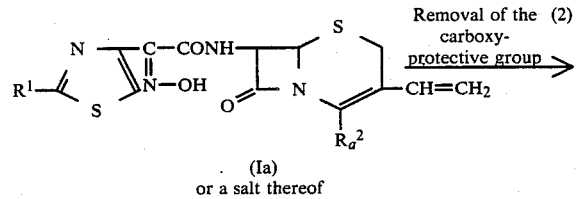

(Ib)
or a salt thereof

Process 3:

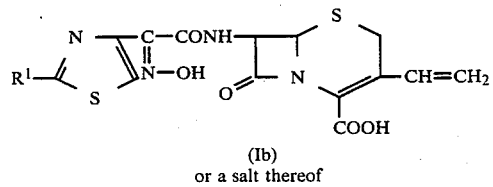

(Ib)
or a reactive derivative at the carboxy group thereof, or a salt thereof

-continued

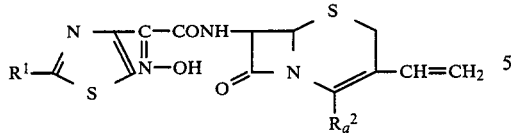

(Ia)
or a salt thereof

Process 4:

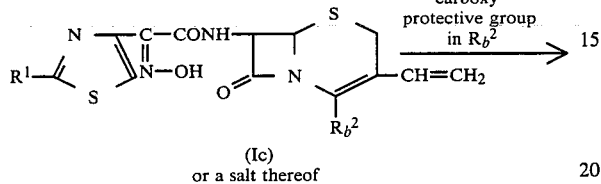

(Ic)
or a salt thereof

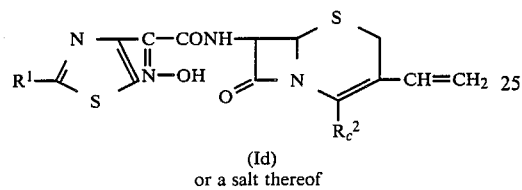

(Id)
or a salt thereof in which
R¹ and R² are each as defined above,
X is halogen,
$R_a^2$ is a protected carboxy group,
$R_b^2$ is protected carboxy(lower)alkoxycarbonyl, and
$R_c^2$ is carboxy(lower)alkoxycarbonyl.

With regard to the starting compound (II) used in Process 1, said compound (II) is new and can be prepared, for example, by the following processes.

Process A:

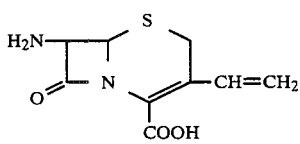

or a reactive derivative at the carboxy group thereof, or a salt thereof

| R—OH
| or a reactive derivative
| at the hydroxy group,
| or a salt thereof

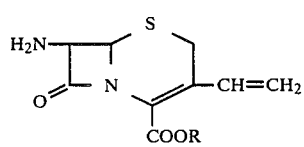 (IV$_b$)

or a salt thereof

Process B:

-continued

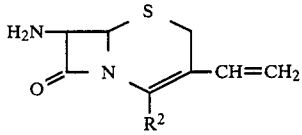 (IV)

or a reactive derivative at the amino group thereof, or a salt thereof

1 | X—CH₂COCH₂COOH (VI)
| or a reactive derivative at the
| carboxy group or a salt thereof

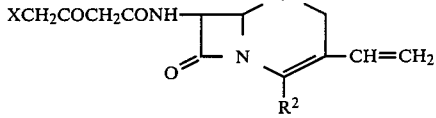 (VII)

or a salt thereof

2 | Nitrosating Agent

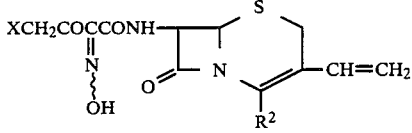 (II)

or a salt thereof in which
R² and X are each as defined above, and
the group "COOR" is a protected carboxy group.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "protected amino" group may include an amino group substituted by a conventional amino-protective group which is used in penicillin and cephalosporin compounds, for example, acyl as mentioned below, ar(lower)alkyl such as mono-(or di or tri)phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), (C₃–C₇)-cycloalkanecarbonyl (e.g. cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "protected carboxy" group and "protected carboxy" moiety in the term "protected carboxy(lower)alkoxycarbonyl" may include an esterified carboxy group which is conventionally used in penicillin or cephalosporin compound.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester, isopropylthiomethyl ester, etc.), carboxy-substituted-lower alkyl ester (e.g. carboxymethyl ester, 2-carboxyethyl ester, 3-carboxypropyl ester, etc.), protected carboxy-substituted-lower alkyl ester such as lower alkoxycarbonyl-substituted-lower alkyl ester (e.g. tert-butoxycarbonylmethyl ester, 2-tert-butoxycarbonylethyl ester, 3-tert-butoxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)pentanoyloxyethyl ester, etc.], higher alkanoyloxy(lower)alkyl ester [e.g. heptanoyloxymethyl ester, octanoyloxymethyl ester, nonanoyloxymethyl ester, decanoyloxymethyl ester, undecanoyloxymethyl ester, lauroyloxymethyl ester, tridecanoyloxymethyl ester, myristoyloxymethyl ester, pentadecanoyloxymethyl ester, palmitoyloxymethyl ester, heptadecanoyloxymethyl ester, stearoyloxymethyl ester, nonadecanoyloxymethyl ester, eicosanoyloxymethyl ester, 1(or 2)-heptanoyloxyethyl ester, 1(or 2)-octanoyloxyethyl ester, 1(or 2)-nonanoyloxyethyl ester, 1(or 2)-decanoyloxyethyl ester, 1(or 2)undecanoyloxyethyl ester, 1(or 2)-lauroyloxyethyl ester, 1(or 2)-tridecanoyloxyethyl ester, 1(or 2)-myristoyloxyethyl ester, 1(or 2)-pentadecanoyloxyethyl ester, 1(or 2)palmitoyloxyethyl ester, 1(or 2)-heptadecanoyloxyethyl ester, 1(or 2)-stearoyloxyethyl ester, 1(or 2)-nonadecanoyloxyethyl ester, 1(or 2)-eicosanoyloxyethyl ester, etc.], lower alkoxycarbonyloxy(lower)alkyl ester [e.g. methoxycarbonyloxymethyl ester, ethoxycarbonyloxymethyl ester, propoxycarbonyloxymethyl ester, isopropoxycarbonyloxymethyl ester, tert-butoxycarbonyloxymethyl ester, 1(or 2)-methoxycarbonyloxyethyl ester, 1(or 2)ethoxycarbonyloxyethyl ester, 1(or 2)-propoxycarbonyloxyethyl ester, 1(or 2)-isopropoxycarbonyloxyethyl ester, 1(or 2)-butoxycarbonyloxyethyl ester, 1(or 2)-isobutoxycarbonyloxyethyl ester, 1(or 2)-tertbutoxycarbonyloxyethyl ester, 1(or 2)-hexyloxycarbonyloxyethyl ester, 1(or 2 or 3)-methoxycarbonyloxypropyl ester, 1(or 2 or 3)-ethoxycarbonyloxypropyl ester, 1(or 2 or 3)-isopropoxycarbonyloxypropyl ester, 1(or 2 or 3 or 4)-ethoxycarbonyloxybutyl ester, 1(or 2 or 3 or 4)butoxycarbonyloxybutyl ester, 1(or 2 or 3 or 4 or 5)pentyloxycarbonyloxypentyl ester, 1 (or 2 or 3 or 4 or 5)neopentyloxycarbonyloxypentyl ester, 1 (or 2 or 3 or 4 or 5 or 6)-ethoxycarbonyloxyhexyl ester, etc.], (5-lower alkyl-2-oxo-1,3-dioxol-4-yl) (lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.], lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

Suitable "halogen" may include chlorine, bromine, iodine, and the like.

Suitable "lower alkoxycarbonyl" group in the terms "protected carboxy(lower)alkoxycarbonyl" and "carboxy(lower)alkoxycarbonyl" may include methoxycarbonyl, ethoxycarbonyl, propoxycarbonyl, and the like.

Suitable "lower alkoxycarbonyloxy(lower)alkyl" group may include methoxycarbonyloxymethyl, ethoxycarbonyloxymethyl, propoxycarbonyloxymethyl, isopropoxycarbonyloxymethyl, tert-butoxycarbonyloxymethyl, 1(or 2)methoxycarbonyloxyethyl, 1(or 2)-ethoxycarbonyloxyethyl, 1(or 2)-propoxycarbonyloxyethyl, 1(or 2)-isopropoxycarbonyloxyethyl, 1(or 2)-butoxycarbonyloxyethyl, 1(or 2)-isobutoxycarbonyloxyethyl, 1(or 2)-tertbutoxycarbonyloxyethyl, 1(or 2)-hexyloxycarbonyloxyethyl, 1(or 2 or 3)-methoxycarbonyloxypropyl, 1(or 2 or 3)ethoxycarbonyloxypropyl, 1(or 2 or 3)-isopropoxycarbonyloxypropyl, 1(or 2 or 3 or 4)-ethoxycarbonyloxybutyl, 1(or 2 or 3 or 4)-butoxycarbonyloxybutyl, 1(or 2 or 3 or 4 or 5)-pentyloxycarbonyloxypentyl, 1-(or 2 or 3 or 4 or 5)neopentyloxycarbonyloxypentyl, 1(or 2 or 3 or 4 or 5 or 6)ethoxycarbonyloxyhexyl, and the like.

Preferable embodiments of the object compound (I) are as follows.

Preferable embodiment of $R^1$ is amino; and $R^2$ is carboxy or esterified carboxy [more preferably carboxy-substituted-lower alkoxycarbonyl, lower alkoxycarbonyl-substituted-lower alkoxycarbonyl, lower alkanoyloxy(lower)alkoxycarbonyl, higher alkanoyloxy(lower)alkoxycarbonyl, lower alkoxycarbonyloxy(lower)alkoxycarbonyl, (5-lower alkyl-2-oxo-1,3-dioxol-4-yl)-(lower)alkoxycarbonyl, ar(lower)alkoxycarbonyl (e.g., diphenyl(lower)alkoxycarbonyl), or phthalidyloxycarbonyl].

The processes for the production of the compound (I) or a salt thereof will be explained in detail as follows.

(1) Process 1

The compound (I) or a salt thereof can be produced by reacting the compound (II) or a salt thereof with the compound (III).

Suitable salt of the compound (II) may include the same salt with a base as exemplified for the compound (I).

This reaction is usually conducted in a conventional solvent which does not adversely influence the reaction such as ethyl acetate, methylene chloride, chloroform, carbon tetrachloride, tetrahydrofuran, N,N-dimethylformamide, N,N-dimethylacetamide, dioxane, water, acetic acid, formic acid, etc. or a mixture thereof.

The reaction temperature is not critical and the reaction is usually conducted under cooling to warming.

Process 2

The compound (Ib) or a salt thereof can be produced by subjecting the compound (Ia) or a salt thereof to the removal reaction of the carboxy-protective group.

Suitable salts of the compounds (Ia) and (Ib) may include the same ones as exemplified for the compound (I).

Suitable method for this removal reaction may include conventional one such as hydrolysis, reduction, or the like.

(i) For hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluensulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

Further, instead of the above acid, Lewis acid such as boron trifluoride, boron trifluoride etherate, alminum trichloride, antimony pentachloride, ferric chloride, stannic chloride, titanium tetrachloride, zinc chloride, and the like can also be used in this reaction, and in case of using Lewis acid, the reaction can preferably be carried out in the presence of cation trapping agent (e.g. anisole).

The hydrolysis is usually conducted in a conventional solvent which does not adversely influence the reaction such as water, methanol, ethanol, propanol, tert-butyl alcohol, tetrahydrofuran, N,N-dimethylformamide, N,N-dimethylacetamide, dioxane or a mixture thereof, and further the above-mentioned acids can also be used as a solvent when they are in liquid.

The reaction temperature of this hydrolysis is not critical, and the reaction is usually conducted under cooling to at somewhat elevated temperature.

(ii) For Reduction

Reduction is conducted in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually conducted in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually conducted under cooling to warming.

Process 3

The compound (Ia) or a salt thereof can be produced by introducing a carboxy-protective group into the compound (Ib) or a reactive derivative at the carboxy group thereof, or a salt thereof.

Suitable reactive derivative at the carboxy group of the compound (Ib) may include conventional one which can be applied to this reaction such as acid halide (e.g. acid chloride, acid bromide, etc.), or the like.

The introducing agent of a carboxy-protective group to be used in this reaction may include a conventional esterifying agent such as an alcohol or its reactive equivalent (e.g. halide, sulfonate, sulfate, diazo compound, etc.), and the like.

The present reaction can also be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, cesium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoate (e.g. sodium acetate, etc.), trialkylamine (e.g. triethylamine, etc.), 1,8-diazabicyclo[5,4,0]undec-7-en, pyridines (e.g. pyridine, lutidine picoline, etc.), quinoline and the like, and can also be carried out in the presence of metal iodide (e.g. sodium iodide, potassium iodide, etc.).

In case that the alcohol is used as the introducing agent of a carboxy-protective group, the reaction can be carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a sulfonic acid esterof N-hydroxybenzotriazole derivative [e.g. 1-(4-chlorobenzenesulfonyloxy)-6-chloro-1H-benzotriazole, etc.], or the like.

This reaction is usually conducted in a solvent which does not adversely influence the reaction such as acetone, dioxane, acetonitrile, chloroform, benzene, methylene chloride, ethylene chloride, tetrahydrofuran, ethyl acetate, dimethylsulfoxide, N,N-dimethylformamide, N,N-dimethylacetamide, pyridine, hexamethylphosphoramide, etc. or a mixture thereof.

The reaction temperature is not critical, and the reaction is in many cases conducted under cooling, at ambient temperature or under heating.

Process 4

The compound (Id) or a salt thereof can be prepared by subjecting the compound (Ic) or a salt thereof to removal reaction of the carboxy-protective group in $R_b^2$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (Ia) in Process 2, and therefore are to be referred to said explanation.

The object compound (I) can be converted into its pharmaceutically acceptable salt in a conventional manner.

The processes for the preparation of the starting compound are explained in detail in the following.

Process A

The compound (IVb) or a salt thereof can be produced by reacting the compound (IVa) or a reactive derivative at the carboxy group thereof, or a salt thereof with the compound (V) or a reactive derivative at the hydroxy group, or a salt thereof.

Suitable reactive derivative at the carboxy group of the compound (IVa) may include the same ones as exemplified for the compound (Ib) in Process 3.

Suitable reactive derivative at the hydroxy group of the compound (V) may include the compound (V) whose hydroxy group is substituted by an acid residue such as halogen (e.g. chlorine, bromine, iodine, etc.), or the like.

Suitable salts of the compounds (IVa) and (IVb) may include the same salt as exemplified for the compound (I), and suitable salt of the compound (V) may include the same salt with a base as exemplified for the compound (I).

This reaction is carried out by the same method as that illustrated for Process 3, and therefore, the reaction conditions (e.g. reaction temperature, solvent, base, etc.) are to be referred to said explanation.

Process B— 1

The compound (VII) or a salt thereof can be produced by reacting the compound (IV) or a reactive derivative at the amino group thereof, or a salt thereof with the compound (VI) or a reactive derivative at the carboxy group thereof or a salt thereof.

Suitable reactive derivative at the amino group of the compound (IV) may include a conventional one, for example, a silyl derivative formed by the reaction of the compound (IV) with a silyl compound such as trimethylsilylacetamide, bis(trimethylsilyl)acetamide, bis(trimethylsilyl)urea, and the like, and suitable reactive derivative of the compound (VI) may include an acid halide such as acid chloride, acid bromide, or the like, which can be prepared by the reaction of diketene and halogen.

Suitable salt of the compound (IV) may include the same salt as exemplified for the compound (I), and suitable salts of the compounds (VI) and (VII) may include the same salt with a base as exemplified for the compound (I).

The reaction is usually conducted in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

The reaction temperature is not critical and the reaction is usually conducted under cooling to warming.

Process B— 2

The compound (II) or a salt thereof can be produced by reacting the compound (VII) or a salt thereof with a nitrosating agent.

Suitable nitrosating agent may include nitrous acid and its conventional derivatives such as nitrosyl halide (e.g. nitrosyl chloride, nitrosyl bromide, etc.), alkali metal nitrite (e.g. sodium nitrite, potassium nitrite, etc.), alkyl nitrite (e.g. butyl nitrite, pentyl nitrite, isoamyl nitrate, etc.), and the like.

In case that a salt of nitrous acid or its alkali metal salt is used as a nitrosating agent, the reaction is preferably carried out in the presence of an acid such as an inorganic or organic acid (e.g. hydrochloric acid, sulfuric acid, formic acid, acetic acid, etc.).

This reaction can preferably be carried out in the presence of an activated methylene compound such as acetylacetone, ethyl acetoacetate, and the like.

This reaction is usually conducted in a conventional solvent which does not adversely influence the reaction such as water, acetic acid, benzene, methanol, ethanol, tetrahydrofuran, methylene chloride, or a mixture thereof. The reaction temperature is not critical and the reaction is preferably conducted within the range of cooling to an ambient temperature.

The compound (II) of this reaction may include syn isomer, anti isomer and a mixture thereof at the hydroxyimino group thereof, and such compound may be represented by the partial formula:

The object compound (I) and the pharmaceutically acceptable salt thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration.

Now in order to show the utility of the object compound (I), the test data on the urinary excretion of a representative compound (I) of this invention are shown in the following.

Urinary Excretion Test (1) Test Method

Test compound (100 mg/kg) was given orally to groups of three rats, and urinary samples were collected at 0 to 24 hours.

(2) Test Compound (A) Pivaloyloxymethyl 7-[2-(2-aminothiazol-4-yl)-2-hydroxyiminoacetamido]-3-vinyl-3-cephem-4-carboxylate (syn isomer) (hereinafter referred to as Compound A)

(B) 1-DL-Ethoxycarbonyloxyethyl 7-[2-(2-aminothiazol-4-yl)-2-hydroxyiminoacetamido]-3-vinyl-3-cephem-4-carboxylate (syn isomer) (hereinafter referred to as Compound B)

(3) Test Result

Percentage of urinary excretion value is shown in the following table.

| Compound | Urinary Excretion (%) |
|---|---|
| A | 54.09 |
| B | 26.0 |

For therapeutic administration, the object compound (I) and the pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound (I) of the present invention may be used in treating diseases infected by pathogenic microorganisms.

The following Preparations and Examples are given for the purpose of illustrating the present invention.

Preparation 1

1-DL-Iodoethyl ethyl carbonate (7.32 g) was added all at once to a solution of 7-amino-3-vinyl-3-cephem-4-carboxylic acid (4.52 g) and 1,8-Diazabicyclo[5,4,0]undec-7-en (4.5 ml) in N,N-dimethylacetamide (45 ml) under ice-cooling. After the mixture was stirred for 45 minutes at 0°-3° C., the reaction mixture was poured into ice-water (200 ml) and extracted with ethyl acetate (200 ml). The organic extract was washed with water and brine, dried over magnesium sulfate and concentrated to one fourth volume of its original one. The concentrate was added to concentrated hydrochloric acid (2 ml). The resulting precipitate was collected by filtration, washed with ethyl acetate and air-dried to give DL-1-ethoxycarbonyloxyethyl 7-amino-3-vinyl-3-cephem-4-carboxylate hydrochloride (2.66 g).

IR (Nujol) cm$^{-1}$: 3400, 1775, 1755, 1720

NMR (DMSO-d$_6$) δ: 1.27 (3H, , J=7 Hz), 1.53 (3H, d, J=6 Hz), 3.93 (2H, m), 4.23 (2H, q, J=7 Hz), 5.0–6.0 (4H, m), 6.7–7.2 (2H, m), 8.0–10.0 (2H, broad m).

Preparation 2

Benzhydryl 7-amino-3-vinyl-3-cephem-4-carboxylate hydrochloride (150 g) and trimethylsilylacetamide (189 g) was dissolved in ethyl acetate (1.5 liter), and the solution was cooled to −20° C. Thereto was added 4-bromoacetoacetic bromide, which was obtained from diketene (39 g) and bromine (75 g) in methylene chloride (200 ml) at −20° C., and the mixture was stirred at −10° C. for an hour. The reaction mixture was poured into a mixture of methylene chloride (2 liter) and water (1 liter), and the organic layer was separated, followed by washing with water and an aqueous sodium chloride. After the solvent was removed in vacuo, the resultant precipitates were washed with ethyl acetate and then dried to give benzhydryl 7-(4-bromoacetoacetamido)-3-vinyl-3-cephem-4-carboxylate (171 g), mp 133°–137° C. (dec.).

IR (Nujol) cm$^{-1}$: 3270, 1765, 1705, 1650, 1550

NMR (DMSO-d$_6$) δ: 3.5–4.5 (6H, m), 5.2–6.0 (4H, m), 6.83 (1H, m), 7.00 (1H, s), 7.45 (10H, m), 9.25 (1H, d, J=8 Hz)

Preparation 3

The following compound was obtained according to a similar manner to that of Preparation 2.

DL-1-Ethoxycarbonyloxyethyl 7-(4-bromoacetoacetamido)-3-vinyl-3-cephem-4-carboxylate IR (Nujol) cm$^{-1}$: 1780, 1760, 1270, 1080

NMR (DMSO-d$_6$) δ: 1.27 (3H, t, J=7 Hz), 1.53 (3H, d, J=6 Hz), 3.93 (2H, m), 4.17 (2H, s), 4.23 (2H, q, J=7 Hz), 4.33 (2H, s), 5.0–6.0 (4H, m), 6.5–7.2 (2H, m), 9.17 (1H, d, J=8 Hz)

Preparation 4

To a solution of benzhydryl 7-(4-bromoacetoacetamido)-3-vinyl-3-cephem-4-carboxylate (40 g) in methylene chloride (400 ml) and acetic acid (200 ml) was added dropwise a solution of sodium nitrite (7.5 g) in water (50 ml) at −10° to −5° C., and the mixture was stirred at −5° C. for 30 minutes. After addition of urea (7 g) and stirring at ambient temperature for 30 minutes, water (400 ml) was added to the reaction mixture. The organic layer was separated, washed with water and 10% aqueous sodium chloride, and dried over magnesium sulfate.

Removal of the solvent gave the solid, which was dried in vacuo to obtain benzhydryl 7-(4-bromo-2-hydroxyiminoacetoacetamido)-3-vinyl-3-cephem-4-carboxylate (48 g), mp 105°–108° C.

IR (Nujol) cm$^{-1}$: 3250, 1770, 1705, 1655, 1540

NMR (DMSO-d$_6$) δ: 3.80 (2H, m), 4.67 (2H, s), 5.2–6.2 (4H, m), 6.80 (1H, m), 7.00 (1H, s), 7.45 (10H, m), 9.42 (1H, d, J=8 Hz), 13.20 (1H, s)

EXAMPLE 1

To a solution of benzhydryl 7-(4-bromo-2-hydroxyiminoacetoacetamido)-3-vinyl-3-cephem-4-carboxylate (48 g) in N,N-dimethylacetamide (200 ml) was added thiourea (7.0 g) at 5° C., and the mixture was stirred at ambient temperature for an hour. After the reaction mixture was poured into 3% aqueous sodium bicarbonate (2 liter), sodium chloride (150 g) was added thereto. The precipitates were collected by filtration and then dissolved in a mixture of acetone (200 ml) and ethyl acetate (500 ml). The separated organic layer was washed with an aqueous sodium chloride, followed by evaporation. The resultant precipitates were collected by filtration, washed with ethyl acetate and diethyl ether and dried in vacuo to give benzhydryl 7-[2-(2-aminothiazol-4-yl)-2-hydroxyiminoacetamido]-3-vinyl-3-cephem-4-carboxylate (syn isomer) (16.9 g), mp 133°–136° C.

IR (Nujol) cm$^{-1}$: 3200, 1780, 1720, 1670, 1610

NMR (DMSO-d$_6$) δ: 3.75 (2H, m), 5.2–6.1 (4H, m), 6.67 (1H, s), 6.75 (1H, m), 7.00 (1H, s), 7.20 (2H, m), 7.34 (10H, m), 9.50 (1H, d, J=8 Hz)

EXAMPLE 2

The following compounds were obtained according to a similar manner to that of Example 1.

(1) DL-1-Ethoxycarbonyloxyethyl 7-[2-(2-aminothiazol-4-yl)-2-hydroxyiminoacetamido]-3-vinyl-3-cephem-4-carboxylate (syn isomer)

IR (Nujol) cm$^{-1}$: 3300, 1780, 1750, 1670

NMR (DMSO-d$_6$) δ: 1.17 (3H, t, J=7 Hz), 1.50 (3H, d, J=6 Hz), 3.75 (2H, m), 4.13 (2H, q, J=7 Hz), 5.1–6.0 (4H, m), 6.63 (1H, s), 6.7–7.3 (4H, m), 9.45 (1H, d, J=8 Hz), 11.33 (1H, s)

(2) t-Butoxycarbonylmethyl 7-[2-(2-aminothiazol-4-yl)-2-hydroxyiminoacetamido]-3-vinyl-3-cephem-4-carboxylate (syn isomer)

IR (Nujol) cm$^{-1}$: 3300, 3170, 1780, 1730, 1665, 1620

(3) DL-1-Propionyloxyethyl 7-[2-(2-aminothiazol-4-yl)-2-hydroxyiminoacetamido]-3-vinyl-3-cephem-4-carboxylate (syn isomer)

IR (Nujol) cm$^{-1}$: 3300, 3200, 1780, 1765, 1720, 1710, 1660, 1630

(4) Pivaloyloxymethyl 7-[2-(2-aminothiazol-4-yl)-2-hydroxyiminoacetamido]-3-vinyl-3-cephem-4-carboxylate (syn isomer)

IR (Nujol) cm$^{-1}$: 3400, 1785, 1750, 1670, 1615, 1530, 1310, 1220

(5) Palmitoyloxymethyl 7-[2-(2-aminothiazol-4-yl)-2-hydroxyiminoacetamido]-3-vinyl-3-cephem-4-carboxylate (syn isomer)

IR (Nujol) cm$^{-1}$: 3300, 1775, 1670, 1615, 1530, 1305, 1210

(6) (5-Methyl-2-oxo-1,3-dioxol-4-yl)methyl 7-[2-(2-aminothiazol-4-yl)-2-hydroxyiminoacetamido]-3-vinyl-3-cephem-4-carboxylate (syn isomer)

IR (Nujol) cm$^{-1}$: 3300, 1812, 1772, 1730, 1668, 1611

(7) Phthalid-3-yl 7-[2-(2-aminothiazol-4-yl)-2-hydroxyiminoacetamido]-3-vinyl-3-cephem-4-carboxylate (syn isomer)

IR (Nujol) cm$^{-1}$: 3200 (broad), 1772 (broad), 1728 (shoulder), 1660, 1620

(8) Carboxymethyl 7-[2-(2-aminothiazol-4-yl)-2-hydroxyiminoacetamido]-3-vinyl-3-cephem-4-carboxylate (syn isomer)

IR (Nujol) cm$^{-1}$: 1765 (broad), 1720, 1660 (broad)

(9) Sodium 7-[2-(2-aminothiazol-4-yl)-2-hydroxyiminoacetamido]-3-vinyl-3-cephem-4-carboxylate (syn isomer)

IR (Nujol) cm$^{-1}$: 3200, 1760, 1660, 1600

EXAMPLE 3

Benzhydryl 7-[2-(2-aminothiazol-4-yl)-2-hydroxyiminoacetamido]-3-vinyl-3-cephem-4-carboxylate (syn isomer) (68.5 g) was added portionwise to a mixture of 2,2,2-trifluoroacetic acid (60 ml) and anisole (60 ml) at 5°–7° C., and the mixture was stirred at 5° C. for an hour. The reaction mixture was added dropwise to diisopropyl ether (1.5 liter), followed by collecting the precipitates by filtration. After dissolving in a mixture of tetrahydrofuran (100 ml) and ethyl acetate (100 ml), the solution was extracted with an aqueous sodium bicarbonate. The obtained aqueous layer was adjusted to pH 5.0 with 10% hydrochloric acid, washed with ethyl acetate and then chromatographed on aluminum oxide. Elution was carried out by 3% aqueous sodium acetate, and the fractions containing the desired compound were collected. After adjusting to pH 6.0 with 10% hydrochloric acid, the aqueous solution was again chromatographed on activated charcoal. Elution was carried out by 20% aqueous acetone, and the collected fractions were concentrated in vacuo and then lyophilized to give sodium 7-[2-(2-aminothiazol-4-yl)-2-hydroxyiminoacetamido]-3-vinyl-3-cephem-4-carboxylate (syn isomer) (14.4 g), which was decomposed from 220° C.

IR (Nujol) cm$^{-1}$: 3200, 1760, 1660, 1600

NMR (D$_2$O) δ: 3.67 (2H, s), 5.2–5.7 (3H, m), 5.83 (1H, d, J=5 Hz), 6.80 (1H, m), 7.00 (1H, s)

EXAMPLE 4

1-DL-Iodoethyl ethyl carbonate (22 g) was added dropwise to a solution of sodium 7-[2-(2-aminothiazol-4-yl)-2-hydroxyiminoacetamido]-3-vinyl-3-cephem-4-carboxylate (syn isomer) (15 g) in N,N-dimethylacetamide (120 ml) at 5°–7° C., and the mixture was stirred at 5° C. for 30 minutes. To the reaction mixture was added ethyl acetate (200 ml), followed by filtration. The filtrate was washed with water and an aqueous sodium chloride, and then dried over magnesium sulfate. After removal of the solvent, the residue was washed with ethyl acetate and dried in vacuo to give DL-1-ethoxycarbonyloxyethyl 7-[2-(2-aminothiazol-4-yl)-2-hydroxyiminoacetamido]-3-vinyl-3-cephem-4-carboxylate (syn isomer) (7.4 g), mp 126°–130° C.

IR (Nujol) cm$^{-1}$: 3300, 1780, 1750, 1670, 1620

NMR (DMSO-d$_6$) δ: 1.17 (3H, t, J=7 Hz), 1.50 (3H, d, J=6 Hz), 3.75 (2H, m), 4.13 (2H, q, J=7 Hz), 5.1–6.0 (4H, m), 6.65 (1H, s), 6.7–7.3 (4H, m), 9.45 (1H, d, J=8 Hz), 11.33 (1H, s)

EXAMPLE 5

Cesium carbonate (2.06 g) was added to a solution of 7-[2-(2-aminothiazol-4-yl)-2-hydroxyiminoacetamido]-3-vinyl-3-cephem-4-carboxylic acid (syn isomer) (5 g) in N,N-dimethylacetamide (50 ml) at 25° C.

The mixture was stirred at ambient temperature for 1 hour and cooled on an ice-bath. To this cooled mixture was added 1-DL-iodoethyl ethyl carbonate (9.2 g) all at once, and the mixture was stirred at 0°–3° C. for 40 minutes. To the reaction mixture was added ethyl acetate (300 ml), which was followed by filtration. The filtrate was washed with water twice and brine, treated with activated charcoal and dried over magnesium sulfate. After removal of the solvent in vacuo, the residue was washed with diisopropyl ether and air-dried to give DL-1-ethoxycarbonyloxyethyl 7-[2-(2-aminothiazol-4-yl)-2-hydroxyiminoacetamido]-3-vinyl-3-cephem-4-carboxylate (syn isomer) (4.6 g), mp 126°–130° C.

IR (Nujol) cm$^{-1}$: 3300, 1780, 1750, 1670

NMR (DMSO-d$_6$) δ: 1.17 (3H, t, J=7 Hz), 1.50 (3H, d, J=6 Hz), 3.75 (2H, m), 4.13 (2H, q, J=7 Hz), 5.1–6.0 (4H, m), 6.63 (1H, s), 6.7–7.3 (4H, m), 9.45 (1H, d, J=8 Hz), 11.33 (1H, s).

EXAMPLE 6

Potassium iodide (4.0 g) was added to a solution of t-butyl chloroacetate (1.2 g) in N,N-dimethylacetamide (50 ml) and the mixture was stirred for 40 minutes at ambient temperature. The precipitate was filtered off. To the filtrate was added potassium 7-[2-(2-aminothiazol-4-yl)-2-hydroxyiminoacetamido]-3-vinyl-3-cephem-4-carboxylate (syn isomer) (3.2 g) at ambient temperature and the mixture was stirred for 1.5 hours at the same temperature. The reaction mixture was added to a mixture of water and ethyl acetate and the mixture was adjusted to pH 7.0 with 20% aqueous solution of potassium carbonate. The separated organic layer was washed with water, dried over magnesium sulfate and evaporated to give t-butoxycarbonylmethyl 7-[2-(2-aminothiazol-4-yl)-2-hydroxyiminoacetamido]-3-vinyl-3-cephem-4-carboxylate (syn isomer) (2.0 g).

IR (Nujol) cm$^{-1}$: 3300, 3170, 1780, 1730, 1665, 1620

NMR (DMSO-d$_6$) δ: 1.43 (9H, s), 3.76 (2H, q, J=18.0 Hz), 4.73 (2H, s), 5.24 (1H, d, J=5.0 Hz), 5.38 (1H, d, J=11.0 Hz), 5.68 (1H, d, J=18.0 Hz), 5.82 (1H, dd, J=5.0 Hz, 8.0 Hz), 6.66 (1H, s), 7.03 (1H, dd, J=11.0 Hz, 18.0 Hz), 9.46 (1H, d, J=8.0 Hz).

EXAMPLE 7

DL-1-Propionyloxyethyl 7-[2-(2-aminothiazol-4-yl)-2-hydroxyiminoacetamido]-3-vinyl-3-cephem-4-carboxylate (syn isomer) (1.38 g) was obtained by reacting 7-[2-(2-aminothiazol-4-yl)-2-hydroxyiminoacetamido]-3-vinyl-3-cephem-4-carboxylic acid (syn isomer) (5 g) with DL-1-bromoethyl propionate (4.56 g) according to a similar manner to that of Example 5.

IR (Nujol) cm$^{-1}$: 3300, 3200, 1780, 1765, 1720, 1710, 1660, 1630

NMR (DMSO-d$_6$) δ: 1.03 (3H, t, J=7 Hz), 1.48 (3H, d, J=6 Hz), 2.38 (2H, q, J=7 Hz), 3.53 and 3.97 (2H, ABq, J=18 Hz), 5.23 (1H, d, J=5 Hz), 5.4 (1H, d, J=11 Hz), 5.65 (1H, d, J=18 Hz), 5.85 (1H, dd, J=8 Hz, 5 Hz), 6.67 (1H, s), 6.83 (1H, dd, J=18 Hz, 11 Hz), 6.93 (1H, q, J=6 Hz), 7.1 (2H, broad s), 9.43 (1H, d, J=8 Hz), 11.33 (1H, s).

EXAMPLE 8

Pivaloyloxymethyl 7-[2-(2-aminothiazol-4-yl)-2-hydroxyiminoacetamido]-3-vinyl-3-cephem-4-carboxylate (syn isomer) (1.24 g) was obtained by reacting 7-[2-(2-aminothiazol-4-yl)-2-hydroxyiminoacetamido]-3-vinyl-3-cephem-4-carboxylic acid (syn isomer) (3 g) with iodomethyl pivalate (5.05 g) according to a similar manner to that of Example 5, mp 90°–100° C. (dec.).

IR (Nujol) cm$^{-1}$: 3400, 1785, 1750, 1670, 1615, 1530, 1310, 1220

NMR (DMSO-d$_6$) δ: 1.14 (9H, s), 3.58 and 3.97 (2H, ABq, J=18 Hz), 5.24 (1H, d, J=5 Hz), 5.39 (1H, d, J=11 Hz), 5.7–6.0 (3H, m), 5.77 (1H, d, J=17 Hz), 6.70 (1H, s), 6.83 (1H, dd, J=11 Hz, 17 Hz), 7.12 (2H, broad s), 9.49 (1H, d, J=8 Hz), 16.24 (1H, s)

EXAMPLE 9

Palmitoyloxymethyl 7-[2-(2-aminothiazol-4-yl)-2-hydroxyiminoacetamido]-3-vinyl-3-cephem-4-carboxylate (syn isomer) (1.86 g) was obtained by reacting 7-[2-(2-aminothiazol-4-yl)-2-hydroxyiminoacetamido]-3-vinyl-3-cephem-4-carboxylic acid (syn isomer) (3 g) with iodomethyl palmitate (4.13 g) according to a similar manner to that of Example 5, mp 90°–105° C. (dec.)

IR (Nujol) cm$^{-1}$: 3300, 1775, 1670, 1615, 1530, 1305, 1210

NMR (DMSO-d$_6$) δ: 1.1–1.7 (26H, m), 2.3–2.5 (2H, m), 3.56 and 3.95 (2H, ABq, J=18 Hz), 5.21 (1H, d, J=5 Hz), 5.37 (1H, d, J=11 Hz), 5.7–6.0 (3H, m), 5.75 (1H, d, J=17 Hz), 6.66 (1H, s), 6.7–7.0 (1H, m)

EXAMPLE 10

To a solution of potassium 7-[2-(2-aminothiazol-4-yl)-2-hydroxyiminoacetamido]-3-vinyl-3-cephem-4-carboxylate (syn isomer) (2.0 g) in N,N-dimethylacetamide (30 ml) was added 4-bromomethyl-5-methyl-1,3-dioxol-2-one (1.0 g) under ice-cooling with stirring. The reaction mixture was stirred at the same temperature for 30 minutes. The resulting mixture was poured into ethyl acetate (200 ml) and the organic solution was washed with water three times. The separated organic layer was dried over magnesium sulfate and concentrated under reduced pressure. The residue was subjected to column chromatography on silica gel (50 g) to give (5-methyl-2-oxo-1,3-dioxol-4-yl)methyl 7-[2-(2-aminothiazol-4-yl)-2-hydroxyiminoacetamido]-3-vinyl-3-cephem-4-carboxylate (syn isomer) (0.62 g).

IR (Nujol) cm$^{-1}$: 3300, 1812, 1772, 1730, 1668, 1611

NMR (DMSO-d$_6$) δ: 2.17 (3H, s), 3.52, 3.98 (2H, ABq, J=17 Hz), 5.15 (2H, s), 5.20 (1H, d, J=5 Hz), 5.30 (1H, d, J=11 Hz), 5.63 (1H, d, J=17 Hz), 5.76 (1H, dd, J=5 Hz, 8 Hz), 6.63 (1H, s), 6.83 (1H, dd, J=11 Hz, 17Hz), 9.42 (1H, d, J=8 Hz), 11.3 (1H, s).

EXAMPLE 11

Phthalid-3-yl 7-[2-(2-aminothiazol-4-yl)-2-hydroxyiminoacetamido]-3-vinyl-3-cephem-4-carboxylate (syn isomer) (1.05 g) was obtained by reacting potassium 7-[2-(2-aminothiazol-4-yl)-2-hydroxyiminoacetamido]-3-vinyl-3-cephem-4-carboxylate (syn isomer) (1.0 g) with 3-bromophthalide (0.9 g) according to a similar manner to that of Example 10.

IR (Nujol) cm$^{-1}$: 3200 (broad), 1772 (broad), 1728 (shoulder), 1660, 1620

NMR (DMSO-d$_6$) δ: 3.70 (2H, m), 5.18 (1H, d, J=5 Hz), 5.43 (1H, d, J=11 Hz), 5.73 (1H, d, J=17 Hz), 5.83 (1H, dd, J=5 Hz, 8 Hz), 6.75 (1H, s), 6.7–7.2 (2H, m), 7.66–8.0 (6H, m), 9.87 (1H, d, J=8 Hz)

EXAMPLE 12

Trifluoroacetic acid (5.4 ml) was added to a suspension of t-butoxycarbonylmethyl 7-[2-(2-aminothiazol-4-yl)-2-hydroxyiminoacetamido]-3-vinyl-3-cephem-4-carboxylate (syn isomer) (1.8 g) in methylene chloride (4 ml) and anisole (1.8 ml) at ambient temperature and the mixture was stirred for 2 hours at the same temperature.

To the resulting solution was added diisopropyl ether and the mixture was stirred. The resulting precipitates were collected by filtration and washed with diisopropyl ether. The precipitates were added to a mixture of ethyl acetate and water and the mixtuer was adjusted to pH 7 with 20% aqueous solution of sodium carbonate under stirring. The separated aqueous layer was adjusted to pH 2.2 with 10% hydrochloric acid under ice-cooling. The precipitate was collected by filtration, washed with ice-water and dried over phosphorus pentoxide in vacuo to give carboxymethyl 7-[2-(2-aminothiazol-4-yl)-2-hydroxyiminoacetamido]-3-vinyl-3-cephem-4-carboxylate (syn isomer) (0.73 g).

IR (Nujol) cm$^{-1}$: 1765 (broad), 1720, 1660 (broad)

NMR (DMSO-d$_6$) δ: 3.76 (2H, q, J=18.0 Hz), 4.76 (2H, s), 5.24 (1H, d, J=5.0 Hz), 5.37 (1H, d, J=11.0 Hz), 5.86 (1H, d, J=17.0 Hz), 7.83 (1H, dd, J=5.0 Hz, 8.0 Hz), 6.69 (1H, s), 6.61–7.67 (3H, m), 9.50 (1H, d, J=8.0 Hz).

EXAMPLE 13

To a solution of DL-1-ethoxycarbonyloxyethyl 7-[2-(2-aminothiazol-4-yl)-2-hydroxyiminoacetamido]-3-vinyl-3-cephem-4-carboxylate (syn isomer) (1 g) in a mixture of ethyl acetate (50 ml) and ethanol (2 ml) was added concentrated hydrochloric acid (0.3 ml) under ice-cooling, and the mixture was stirred for 10 minutes at 0°–3° C. To the solution was added diisopropyl ether (50 ml), and the resulting precipitate was collected by filtration, washed with ethyl acetate and air-dried to give DL-1-ethoxycarbonyloxyethyl 7-[2-(2-aminothiazol-4-yl)-2-hydroxyiminoacetamido]-3-vinyl-3-cephem-4-carboxylate hydrochloride (syn isomer) (0.8 g).

IR (Nujol) cm$^{-1}$: 3100, 1780, 1750, 1640

NMR (DMSO-d$_6$) δ: 1.23 (3H, t, J=7 Hz), 1.53 (3H, d, J=6 Hz), 3.75 (2H, m), 4.20 (2H, q, J=7 Hz), 5.0–6.0 (6H, m), 6.83 (1H, s), 6.7–7.2 (2H, m), 9.7 (1H, d, J=8 Hz), 12.5 (1H, broad s)

EXAMPLE 14

To a solution of benzhydryl 7-(4-bromoacetoacetamido)-3-vinyl-3-cephem-4-carboxylate (10 g) in a mixture of methylene chloride (70 ml) and acetic acid (25 ml) was dropwise added isoamyl nitrite (3.5 ml) at −3° to −5° C. The mixture was stirred for 40 minutes at −5° C., followed by addition of acetylacetone (4 g) and stirring for 30 minutes at 5° C. To the reaction mixture was added thiourea (3 g) and after stirring for 3 hours, thereto were added dropwise ethyl acetate (70 ml) and diisopropyl ether (100 ml). The resultant precipitate was collected by filtration and dried in vacuo to give benzhydryl 7-[2-(2-aminothiazol-4-yl)-2-hydroxyiminoacetamido]-3-vinyl-3-cephem-4-carboxylate hydrobromide (syn isomer) (11.7 g). 3 g of this product was added portionwise to a mixture of 2,2,2-trifluoroacetic acid (5 ml) and anisole (5 ml) at 5° to 7° C. After stirring for 1 hour at 5° C., the reaction mixture was added dropwise to diisopropyl ether (150 ml). The resultant precipitate was collected by filtration and dissolved in a mixture of tetrahydrofuran (10 ml) and ethyl acetate (10 ml). The organic layer was extracted with an aqueous sodium bicarbonate. The aqueous extract was washed with ethyl acetate under keeping the pH value at 5 and then adjusted to pH 2.2 with 10% hydrochloric acid. This solution was stirred for 1 hour at 0° C., and the obtained crystals were collected by filtration and dried in vacuo to give 7-[2-(2-aminothiazol-4-yl)-2-hydroxyiminoacetamido]-3-vinyl-3-cephem-4-carboxylic acid (syn isomer) (0.79 g).

IR (Nujol) cm$^{-1}$: 3300, 1780, 1665, 1180, 1130

EXAMPLE 15

To a solution of benzhydryl 7-(4-bromoacetoacetamido)-3-vinyl-3-cephem-4-carboxylate (15 g) in a mixture of methylene chloride (100 ml) and acetic acid (30 ml) was added dropwise a solution of sodium nitrite (2.8 g) in water (5 ml) at −10° to −15° C. The reaction mixture was stirred for 40 minutes at −5° C., followed by addition of acetylacetone (4 g) and then stirring for further 15 minutes at ambient temperature. The reaction mixture was poured into a mixture of water (200 ml) and methylene chloride (200 ml), and the organic layer was separated and washed with water. The solution was evaporated and the residue was dissolved in N,N-dimethylacetamide (40 ml). To this solution was added thiourea (3.4 g), and the mixture was stirred for 1 hour at ambient temperature, and poured into a mixture of tetrahydrofuran (150 ml), ethyl acetate (300 ml) and water (300 ml). The mixture was adjusted to pH 6.0 with 20% aqueous sodium hydroxide. The separated organic layer was washed with 20% aqueous sodium chloride successively and dried over magnesium sulfate. The solvent was removed by distillation in vacuo, and the precipitate was collected by filtration and washed with ethyl acetate and diisopropyl ether. This precipitate was dried in vacuo to give benzhydryl 7-[2-(2-aminothiazol-4-yl)-2-hydroxyiminoacetamido]-3-vinyl-3-cephem-4-carboxylate (syn isomer) (8.5 g).

IR (Nujol) cm$^{-1}$: 3200, 1780, 1720, 1670, 1610

EXAMPLE 16

To a solution of benzhydryl 7-[2-(2-aminothiazol-4-yl)-2-hydroxyiminoacetamido]-3-vinyl-3-cephem-4-carboxylate (syn isomer) (5 g) in a mixture of anisole (20 ml) and acetic acid (5 ml) was added dropwise boron trifluoride etherate (5 ml) at 10° C. After stirring for 20 minutes at 10° C., the reaction mixture was poured into a mixture of tetrahydrofuran (100 ml), ethyl acetate (100 ml) and water (100 ml), and then adjusted to pH 6.0 with 20% aqueous sodium hydroxide. The resultant aqueous layer was separated and washed with ethyl acetate under keeping the pH value at 6.0. This solution was subjected to chromatography on aluminum oxide. The fractions eluted with 3% aqueous sodium acetate were collected and adjusted to pH 4.0 with 10% hydrochloric acid. This solution was further chromatographed on nonionic adsorption resin "Diaion HP-20" (Trademark, manufactured by Mitsubishi Chemical Industries). The fractions eluted with 20% aqueous acetone were collected, concentrated in vacuo and adjusted to pH 2.0 with 10% hydrochloric acid. The resultant precipitate was collected by filtration and dried in vacuo to give 7-[2-(2-aminothiazol-4-yl)-2-hydroxyiminoacetamido]-3-vinyl-3-cephem-4-carboxylic acid (syn isomer) (1.23 g).

IR (Nujol) cm$^{-1}$: 3300, 1780, 1665, 1180, 1130

NMR (DMSO-d$_6$) δ: 3.76 (2H, ABq, J=18 Hz), 5.2–6.0 (4H, m), 6.73 (1H, s), 6.8–7.50 (3H, m), 9.5 (1H, d, J=8 Hz), 11.4 (1H, broad s)

EXAMPLE 17

(1) Benzhydryl 7-amino-3-vinyl-3-cephem-4-carboxylate hydrochloride (1 kg) and 1,3-bis(trimethylsilyl)urea (1.46 kg) was dissolved in tetrahydrofuran (8 l) and the mixture was cooled to −20° C. To this solution was added 4-bromoacetoacetyl bromide obtained from diketene (224 ml) and bromine (147 ml) in methylene chloride at −20° C. and the mixture was stirred for 30 minutes at −15° C. The reaction mixture was poured into a mixture of ethyl acetate (12 l) and water (6 l). The organic layer was separated, washed with an aqueous sodium chloride, and then evaporated in vacuo. The resultant precipitate was stirred in diisopropyl ether (10 l) for 1 hour at 0° C., and the obtained crystals were collected by filtration and dried in vacuo to give benzhydryl 7-(4-bromoacetoacetamido)-3-vinyl-3-cephem-4-carboxylate (1.27 kg), mp 133°–137° C. (dec.).

(2)

To a solution of benzhydryl 7-(4-bromoacetoacetamido)-3-vinyl-3-cephem-4-carboxylate (500 g) in a mixture of methylene chloride (4.5 l) and acetic acid (1.7 l) was added dropwise a solution of sodium nitrite (93.2 g) in water (450 ml) at −15° to −22° C. The reaction mixture was stirred for 7 minutes at −15° C., followed by addition of ethyl acetoacetate (117 g) and then stirring for 5 minutes at ambient temperature. The reaction mixture was washed with water (6 l×2) and an aqueous sodium chloride (6 l). To the separated organic layer was added thiourea (82.2 g) dissolved in N,N-dimethylacetamide (1 l), and the mixture was stirred for 1 hour at 36° C. After methylene chloride was removed in vacuo, the residual oil was poured into a mixture of tetrahydrofuran (3.5 l), ethyl acetate (7 l) and ice-water (4 l). This mixture was adjusted to pH 6.0 with 10% aqueous sodium hydroxide. The separated organic layer was washed with water (4 l×2) and an aqueous sodium chloride. The solvent was removed by distillation in vacuo and the residual crystals were stirred in a mixture of ethyl acetate (1.6 l) and diisopropyl ether (2.4 l) for 1 hour at 0° C. The crystals obtained were collected by filtration to give benzhydryl 7-[2-(2-aminothiazol-4-yl)-2-hydroxyiminoacetamido]-3-vinyl-3-cephem-4-carboxylate (syn isomer) (394.5 g).

IR (Nujol)cm$^{-1}$: 3200, 1780, 1720, 1670, 1610

EXAMPLE 18

DL-1-Acetoxyethyl 7[2-(2-aminothiazol-4-yl)-2-hydroxyiminoacetamido]-3-vinyl-3-cephem-4-carboxylate (syn isomer) (1.12 g) was obtained by reacting 7-[2-(2-aminothiazol-4-yl)-2-hydroxyiminoacetamido]-3-vinyl-3-cephem-4-carboxylic acid (syn isomer) (5 g) with DL-1-bromoethyl acetate (3.42 g) in the presence of cesium carbonate (2.04 g) according to a similar manner to that of Example 5.

I.R. (Nujol)cm$^{-1}$: 3300, 1780, 1760, 1670, 1210

What we claim is:

1. A syn isomer of the compound of the formula:

$$R^1 \underset{S}{\overset{N}{\bigvee}} \overset{C-CONH}{\underset{N-OH}{||}} \cdots \overset{S}{\underset{O}{\bigvee}} \overset{}{\underset{R^2}{N}} CH=CH_2 \quad (I)$$

in which
R$^1$ is amino or a protected amino group, and
R$^2$ is carboxy or a protected carboxy group,
and a pharmaceutically acceptable salt thereof.

2. A compound of claim 1, wherein R$^1$ is amino.

3. A compound of claim 2, which is 7-[2-(2-aminothiazol-4-yl)-2-hydroxyiminoacetamido]-3-vinyl-3-cephem-4-carboxylic acid (syn isomer) or its sodium salt or its potassium salt.

4. A compound of claim 2, wherein R$^2$ is esterified carboxy group.

5. A compound of claim 4, wherein R$^2$ is lower alkoxycarbonyloxy(lower)alkoxycarbonyl.

6. A compound of claim 5, which is 1-ethoxycarbonyloxyethyl 7-[2-(2-aminothiazol-4-yl)-2-hydroxyiminoacetamido]-3-vinyl-3-cephem-4-carboxylate (syn isomer) or its hydrochloride.

7. A compound of claim 4, wherein R$^2$ is lower alkoxycarbonyl(lower)alkoxycarbonyl.

8. A compound of claim 7, which is tert-butoxycarbonylmethyl 7-[2-(2-aminothiazol-4-yl)-2-hydroxyiminoacetamido]-3-vinyl-3-cephem-4-carboxylate (syn isomer).

9. A compound of claim 4, wherein R$^2$ is carboxy(lower)alkoxycarbonyl.

10. A compound of claim 9, which is carboxymethyl 7-[2-(2-aminothiazol-4-yl)-2-hydroxyiminoacetamido]-3-vinyl-3-cephem-4-carboxylate (syn isomer).

11. A compound of claim 4, wherein R$^2$ is lower alkanoyloxy(lower)alkoxycarbonyl.

12. A compound of claim 11, which is 1-propionyloxyethyl 7-[2-(2-aminothiazol-4-yl)-2-hydroxyiminoacetamido]-3-vinyl-3-cephem-4-carboxylate (syn isomer).

13. A compound of claim 11, which is pivaloyloxymethyl 7-[2-(2-aminothiazol-4-yl)-2-hydroxyiminoacetamido]-3-vinyl-3-cephem-4-carboxylate (syn isomer).

14. A compound of claim 4, wherein R$^2$ is higher alkanoyloxy(lower)alkoxycarbonyl.

15. A compound of claim 14, which is palmitoyloxymethyl 7-[2-(2-aminothiazol-4-yl)-2-hydroxyiminoacetamido]-3-vinyl-3-cephem-4-carboxylate (syn isomer).

16. A compound of claim 4, wherein R$^2$ is (5-lower alkyl-2-oxo-1,3-dioxol-4-yl) (lower)alkoxycarbonyl.

17. A compound of claim 16, which is (5-methyl-2-oxo-1,3-dioxol-4-yl)methyl 7-[2-(2-aminothiazol-4-yl)-2-hydroxyiminoacetamido]-3-vinyl-3-cephem-4-carboxylate (syn isomer).

18. A compound of claim 4, wherein R$^2$ is phthalidyloxycarbonyl.

19. A compound of claim 18, which is phthalid-3-yl 7-[2-(2-aminothiazol-4-yl)-2-hydroxyiminoacetamido]-3-vinyl-3-cephem-4-carboxylate (syn isomer).

20. A pharmaceutical antimicrobial composition which comprises an antimicrobially effective amount of a compound of claim 1 and a pharmaceutically acceptable salt thereof in admixture with pharmaceutically acceptable carriers.

* * * * *

UNITED STATES PATENT AND TRADEMARK OFFICE

CERTIFICATE EXTENDING PATENT TERM
UNDER 35 U.S.C. § 156

PATENT NO. : 4,559,334

ISSUED : December 17, 1985

INVENTORS : Takao Takaya et al.

PATENT OWNER : Fujisawa Phramaceutical Co., Ltd.

PRODUCT : OMNICEF TABLETS® (cefdinir)

This is to certify that an application under 35 U.S.C. § 156 has been filed in the U.S. Patent and Trademark Office, requesting extension of the term of U.S. Patent No. 4,559,334 based upon the regulatory review of the product OMNICEF TABLETS® (cefdinir) by the Food and Drug Administration. Since it appears that the requirements of the law have been met, this certificate extends the term of the patent for the period of 1,601 days from December 17, 2002, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

Q. Todd Dickinson
Under Secretary of Commerce for Intellectual Property and
Director of the United States Patent and Trademark Office